US011376279B2

(12) United States Patent
Chen et al.

(10) Patent No.: US 11,376,279 B2
(45) Date of Patent: Jul. 5, 2022

(54) BIOMARKERS FOR JOINT AILMENTS AND USES THEREOF

(71) Applicant: Novus International, Inc., St. Charles, MO (US)

(72) Inventors: Juxing Chen, Chesterfield, MO (US); Karen Wedekind, St. Peters, MO (US); Mercedes Vazquez-Anon, Chesterfield, MO (US)

(73) Assignee: Novus International, Inc., St. Charles, MO (US)

( * ) Notice: Subject to any disclaimer, the term of this patent is extended or adjusted under 35 U.S.C. 154(b) by 0 days.

(21) Appl. No.: 16/816,766

(22) Filed: Mar. 12, 2020

(65) Prior Publication Data

US 2020/0289555 A1    Sep. 17, 2020

Related U.S. Application Data

(60) Provisional application No. 62/817,121, filed on Mar. 12, 2019.

(51) Int. Cl.
| | | |
|---|---|---|
| A61K 33/30 | (2006.01) | |
| A61P 19/02 | (2006.01) | |
| G01N 33/68 | (2006.01) | |
| A61K 31/198 | (2006.01) | |
| A61K 33/34 | (2006.01) | |
| A61K 33/32 | (2006.01) | |

(52) U.S. Cl.
CPC .......... *A61K 33/30* (2013.01); *A61K 31/198* (2013.01); *A61K 33/32* (2013.01); *A61K 33/34* (2013.01); *A61P 19/02* (2018.01); *G01N 33/6893* (2013.01); *G01N 2333/575* (2013.01); *G01N 2333/78* (2013.01); *G01N 2800/10* (2013.01)

(58) Field of Classification Search
CPC ...... A61B 2017/00796; A61B 2505/05; A61B 5/1073; A61B 5/4312; A61B 5/6823; A61B 5/708; A61B 90/17; A61K 31/198; A61K 33/30; A61K 33/32; A61K 33/34; A61P 19/02; G01N 2333/575; G01N 2333/78; G01N 2800/10; G01N 33/6893
See application file for complete search history.

(56) References Cited

U.S. PATENT DOCUMENTS

2014/0142861 A1    5/2014   Hagstrom

FOREIGN PATENT DOCUMENTS

| WO | WO-2008154178 A1 * | 12/2008 | ............ A23L 33/12 |
| WO | WO-2008156865 A2 * | 12/2008 | ............ A61P 29/00 |
| WO | 2020186057 A1 | 9/2020 | |

OTHER PUBLICATIONS

Zhao et al. (J Vet Sci 2015;16(4):439-446). (Year: 2015).*

(Continued)

*Primary Examiner* — Ernst V Arnold
(74) *Attorney, Agent, or Firm* — Polsinelli PC

(57) ABSTRACT

The present invention relates to biomarkers that are associated with joint disorders, and methods of using the biomarkers diagnose joint ailments, monitor the progression of joint ailments, determine when treatments is indicated, and monitor the efficiency of treatment. Also provided are methods for treating joint ailments, which comprise administering chelated trace minerals to animals diagnosed with or predisposed to having joint ailments.

8 Claims, 7 Drawing Sheets

(56) References Cited

OTHER PUBLICATIONS

Wedekind et al. (Open Access Animal Physiology 2015;7:13-27). (Year: 2015).*

Rheumatoid Arthritis (RA) Causes and Risk Factors [online] retrieved on Feb. 8, 2021 from: https://www.webmd.com/rheumatoid-arthritis/the-causes-of-rheumatoid-arthritis; 4 pages). (Year: 2021).*

Stavrakakis et al. (Validation of Lameness and joint inflammatory response biomarkers in growing pigs. Recent advances in animal welfare science V UFAW Animal Welfare Conference Jun. 2016; 2 pages) (Year: 2016).*

Bach, Association between chelated trace mineral supplementation and milk yield, reproductive performance, and lameness in dairy cattle, Livestock Sci, 2015, 182:69-75.

Billinghurst, Evaluation of serum concentrations of biomarkers of skeletal metabolism and results of radiograpy as indicators of severity of osteochondrosis in foals, Am J Vet Res, 2004, 65(2):143-150.

Donabedian, Earily changes in biomarkers of skeletal metabolism and their association to the occurrence of osteochondrosis (OC) in the horse, Equine Vet J, 2008, 40(3):253-9.

Frantz, Use of serum biomarkers to predict the development and severity of osteochondrosis lesions in the distal portion of the femur in pigs, Am J Vet Res, 2010, 71(8):946-52.

Frisbie, Serum biomarker levels for musculoskeletal disease in two- and three-year old racing, Thoroughbred hourses: A prospective study of 130 horses, Equine Veterinary Journal, 2010, 42:643-651.

Kilgallon, Analysis of a collagen II degradation protein C2C and a collagen II formation protein CP II in serum of Asian elephants (*Elephas maximus*), J Zoo Wildl Med, 2015, 46(1):146-9.

Turlo, Revisiting predictive biomarkers of muscoloskeletal injury in thoroughbred racehorses: longitudinal study in polish population, BMC Veterinary Research, 2019, 15:66.

International Search Report and Written Opinion dated May 26, 2020 from related International Application No. PCT/US20/22389, 8 pages.

Frantz, et al., The Effect of Dietary Nutrients on Osteochondrosis Lesions and Cartilage Properties in Pigs, Swine Day, 2006, 135-145.

Grøndalen, Osteochondrosis and Arthrosis in Pigs, Acta Veterinaria Scandinavica, 1974, 15:26-42.

Etterlin, et al., Osteochondrosis, but not lameness, is more frequent among free-range pigs than confined herd-mates, Acta Veterinaria Scandinavica, 2015, 57(63):1-10.

Dewey, et al., Clinical and postmortem examination of sows culled for lameness, Canadian Veterinary Journal, 1993, 34:555-556.

Heinonen, et al., Lameness and fertility of sows and gilts in randomly selected loose-housed herds in Finland, Veterinary Record, 2006, 159:383-387.

De Koning, et al., The influence of dietary restriction before and after 10 weeks of age on osteochondrosis in growing gilts, Journal of Animal Science, 2013, 2013(91):5167-5176.

Canning, et al., Retrospective study of lameness cases in growing pigs associated with joint and leg submissions to a veterinary diagnostic laboratory, Journal of Swine Health and Production, 2019, 27(3):118-124.

Fabà, et al., Effects of supplementing organic microminerals and methionine during the rearing phase of replacement gilts on lameness, growth, and body composition, Journal of Animal Science, 2018, 96:3274-3287.

Fanzone, et al., Causes of lameness in sows euthanized for lameness, 51st Annual Meeting of the American Association of Swine Veterinarians, Mar. 7-10, 2020, Atlanta, GA, 2 pages.

Carlson, et al., Effect of reduced growth rate on the prevalence and severity of osteochondrosis in gilts, American Journal of Veterinary Research, 1988, 49(3), Abstract.

Nakano, et al., Leg weakness and osteochondrosis in swine: A review, Canadian Journal of Animal Science, 1987, 67(4):pp. 883-901.

Quinn, et al., The effect of feeding a diet formulated for developing gilts between 70 kg and ~140kg on lameness indicators and carcass traits, Livestock Science, 2015, 174:87-95.

Ferket, et al., Organic trace minerals and 25-hydroxycholecalciferol affect performance characteristics, leg abnormalities, and biomechanical properties of leg bones of turkeys, Poultry Science, 2009, 88:118-131.

Etterlin, et al., Effects of free-range and confined housing on joint health in a herd of fattening pigs, BMC Veterinary Research, 2014, 10(28):1-14.

De Koning, et al., Associations between osteochondrosis and conformation and locomotive characteristics in pigs, Journal of Animal Science, 2012, 90:4752-4763.

Sørensen, et al., Bone biochemical markers for assessment of bone responses to differentiated phosphorus supply in growing-finishing pigs, Journal of Animal Science, 2018, 96:4693-4703.

Richards, et al., Benefit of Mintrex® P blend of organic trace minerals on breaking strength, ash content, tibial dyschondroplasia, synovitis and pododermatitis in heavy weight tom turkeys, Poultry Science, 2010, 89(E-Suppl 1):30 (abstract).

Ytrehus, et al., Etiology and Pathogenesis of Osteochondrosis, Veterinary Pathology, 2007, 44:429-448.

Wegner, et al., Lameness in fattening pigs—Mycoplasma hyosynoviae, osteochondropathy and reduced dietary phosphorus level as three influencing factors: a case report, Porcine Health Management, 2020, 6(41):1-11.

Clavijo, et al., Lameness / Mycoplasma Technical Paper, Cambridge Technologies, 2017, https://cambridgetechnologies.com/wp-content/uploads/Lameness-Tech-Paper.pdf.

Clavijo, et al., Can we eliminate Mycoplasma hyosynoviae and Mycoplasma hyorhinis? National Hog Farmer, Jan. 3, 2017, Accessed Jul. 28, 2021, 6 pages, https://www.nationalhogfarmer.com/animal-health/can-we-eliminate-mycoplasma-hyosynoviae-and-mycoplasma-hyorhinis.

Aasmundstad, et al., Osteochondrosis in pigs diagnosed with computed tomography: heritabilities and genetic correlations to weight gain in specific age intervals, Animal, 2013, 7(10):1576-1582.

Jørgensen, et al., Pathological and Radiological Investigations on Osteochondrosis in Pigs, Associated with Leg Weakness, J. Vet. Med. A., 1995, 42:489-504.

McCoy, et al., Articular osteochondrosis: a comparison of naturally-occurring human and animal disease, Osteoarthritis and Cartilage, 2013, 21:1638-1647.

Ritter, et al., Review: Effects of Ractopamine Hydrochloride (Paylean) on welfare indicators for market weight pigs, Transl. Anim. Sci., 2017, 1:533-558.

Stavrakakis, et al., Walking kinematics of growing pigs associated with differences in musculoskeletal conformation, subjective gait score and osteochondrosis, Livestock Science, 2014.

Grevenhof, et al., The relationship between growth and osteochondrosis in specific joints in pigs, Livestock Science, 2012, 143:85-90.

Grevenhof, et al., The effects of housing system and feeding level on the joint-specific prevalence of osteochondrosis in fattening pigs, Livestock Science, 2011, 135:53-61.

Van Riet, et al., Impact of nutrition on lameness and claw health in sows, Livestock Science, 2013, 156:24-35.

International Preliminary Report on Patentability from related International application No. PCT/US2020/022389 dated Sep. 23, 2021, 6 pp.

\* cited by examiner

BIOMARKERS FOR JOINT AILMENTS AND USES THEREOF

CROSS-REFERENCE TO RELATED APPLICATIONS

This application claims the benefit of U.S. Provisional Application No. 62/817,121, filed Mar. 12, 2019, which is hereby incorporated by reference in its entirety.

FIELD

The present disclosure relates to biomarkers that are associated with joint disorders and uses thereof.

BACKGROUND

Lameness has been identified as a welfare issue in all livestock species that leads to reduction in productivity and profitability of the farm. The incidence of locomotion disorders has been associated with hoof and limb lesions, neurological disorders, metabolic and infectious disorders and mechanical and structural problems. The incidence of lameness can vary from 5 to 40% in sows and dairy cows, and has been associated with lower reproduction performance, intake, longevity, and increased mortality. After reproductive problems, lameness is the most common reason for sows and dairy cows resulting in premature removal from the herd. Causes of lameness have been mostly associated with osteochondrosis in bone joints, however this is difficult to identify in live animals. Visual gait lameness scores are commonly used to identify lameness in production animals (pigs, cows and chickens). However, this subjective scoring system lacks sensitivity and consistency among scorers and leads to delayed detection of lameness. Earlier detection of lameness improves the opportunity for resolution with nutritional programs. Thus, there is a need for accurate, objective methodologies that will enable earlier identification of lameness. Furthermore, solutions are needed for reducing severity and incidence of lameness such as nutritional intervention.

SUMMARY

One aspect of the present disclosure provides a method for treating or preventing a joint ailment in an animal, the method comprising (a) collecting a blood sample from the animal; (b) determining the level of at least one biomarker present in the blood sample, the biomarker being chosen from osteocalcin, C-terminal telopeptide of type I collagen (CTX-1), procollagen type II C-terminal propeptide (P2CP), C-terminal telopeptide of type II collagen (CTX-2), type II collagen cleavage (C2C), or combination thereof; (c) performing an analysis of the level of the at least one biomarker to determine whether the animal has or is predisposed to having a joint ailment, wherein the analysis includes comparing the level of the at least one biomarker in the blood sample to joint ailment-positive and/or joint ailment-negative reference levels of the at least one biomarker in order to determine if the animal has or is predisposed to having a joint ailment; and (d) administering an effective amount of a metal chelate to the animal if the animal is determined to have or to be predisposed to having a joint ailment.

Other aspects and iterations of the disclosure are described in more detail below.

DETAILED DESCRIPTION

Figure 1:
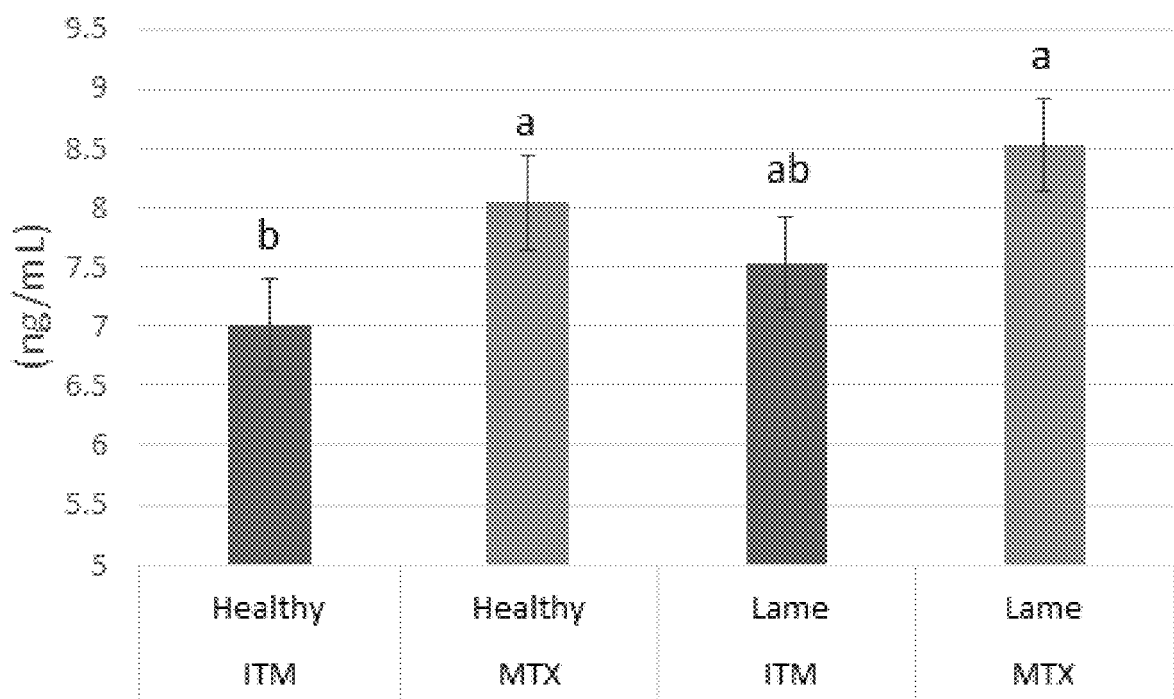
FIG. 1 presents the P2CP concentrations from the four treatments (Healthy ITM, Healthy MTX, Lame ITM, Lame MTX) in the naturally occurring lameness model.

The present disclosure provides biomarkers that may be used as objective indicators of joint ailments in animals, e.g., livestock animals. The biomarkers may be used to diagnose joint ailments, monitor the progression of joint ailments, determine when treatment is indicated, and monitor the efficiency of treatment.

(I) Biomarkers

One aspect of the present disclosure encompasses a panel of serum biomarkers associated with joint ailments. The biomarkers are involved with bone and cartilage synthesis and degradation. The biomarkers may be used to distinguish healthy animals from animals with joint ailments (e.g., lame animals), to monitor the progression of joint ailments or joint diseases, or monitor the efficacy of treatment.

One biomarker is osteocalcin. Also known as bone gamma-carboxyglutamic acid-containing protein (BGLAP), osteocalcin is a noncollagenous protein hormone found in bone and dentin. Osteocalcin is a marker for bone synthesis.

Another biomarker is C-terminal telopeptide of type I collagen or CTX-1, which is a marker for bone degradation or turnover. Type I collagen accounts for about 90% of the organic matrix of bone. CTX-1 relates to bone turnover because it is the portion of the molecule that is cleaved by osteoclasts during bone resorption. CTX1 is a marker for bone degradation.

Still another biomarker is procollagen type II C-terminal propeptide or P2CP, which is a biomarker for cartilage synthesis. Type II collagen is the major organic constituent of cartilage. P2CP is a marker for cartilage synthesis.

A further biomarker is C-terminal telopeptide of type II collagen or CTX-2, which is a biomarker for cartilage degradation. Following the degradation of cartilage, fragments of CTX-2 are released into circulation. CTX2 is a marker for cartilage degradation.

Yet another biomarker is type II collagen cleavage or C2C, which is a biomarker for cartilage degradation.

Upon the determination of levels of the joint ailment biomarkers in healthy animals and animals with joint ailments (either naturally occurring joint ailments or chemically induced joint ailments), these levels may be correlated with standard indicators of lameness or joint ailments to establish biomarker reference levels in healthy animals and animal with joint ailments/lameness. The ratio of synthesis/degradation (P2CP/C2C, P2CP/CTX2, osteocalcin/CTX1) may be associated with lameness.

Standard indicators of lameness or joint ailments include visual gait scores and force plate tests. Gait or locomotion of animals is observed and scored. Gait may be scored on a 5-point scale, ranging from "0" for animals with a normal gait to "4" for animals that are reluctant to walk and bear weight on one or more legs. Force plates may be used to measure the weight of each forelimb, wherein differences suggest that the animal is favoring one limb. By correlating biomarker levels with visual lames/joint ailments standards, reference levels for healthy and lame animals may be established.

(II) Methods for Diagnosing Joint Ailments and/or Monitoring Progression of Joint Ailments Another aspect of the present disclosure provides methods for diagnosing joint ailments in animals and/or monitoring the progression of joint ailments in animals. For example, the methods may be used to distinguish between healthy animals and animals with joint ailments, and if an animal has a joint ailment, the progression of the ailment may be monitored. The methods comprise (a) collecting a blood sample from the animal, (b) determining the level of at least one of the biomarkers disclosed herein that is present in the blood sample; and (c) performing an analysis of the level of the at least one biomarker to determine whether the animal has or is predisposed to having a joint ailment, wherein the analysis includes comparing the levels of the at least one biomarker in the blood sample to joint ailment-positive and/or joint ailment-negative reference levels of the at least one biomarker in order to determine if the animal has or is predisposed to having a joint ailment and/or monitoring the progression of joint ailments in animals known to have joint problems.

Joint Ailments

As used herein, "joint ailments" refer to diseases or disorders of joints or joint tissues. Joint tissues include bone and connective tissue, i.e., cartilage, tendons, and ligaments. Joint ailments include arthritis or osteoarthritis, which are degenerative joint diseases or disorders due to the gradual deterioration of the articular cartilage within one or more the joints. Arthritis is a general description for any condition that causes inflammation in the joints. Rheumatoid arthritis is a chronic inflammatory disorder of the joints. Other joint ailments include osteochondrosis, gouty arthritis, bursitis, tenosynovitis, epicondylitis, synovitis, ankylosing spondylitis, Sjogren's syndrome, psoriatic arthritis, and Lyme disease. Some joint disorders may arise due to hoof or foot pad diseases or disorders.

Step (a)

The first step of the method comprises collecting a blood sample from the animal. Various methods of collecting blood, urine or synovial fluid are known in the art. Generally, a method of collecting blood comprises accessing the blood using a skin-piercing element and collecting the blood therein into some type of a collection device. Accessing the blood may also involve the use of a fluid pathway, a capillary channel (e.g., a capillary tube), a fluid transfer medium (e.g., a hydrophilic porous material), or some kind of mechanical or vacuum means in conjunction with the skin-piercing element. Generally speaking, the sample collection method preferably maintains the integrity of the sample such that abundance values for each molecular feature can be accurately measured. A blood sample may be a whole blood sample, a plasma sample, or a serum sample.

Step (b)

The second step of the method comprises determining the level of at least one biomarker present in the blood sample. A variety of method may be used to determine the level or concentration of the biomarker(s). The biomarker may be detected and quantified using an antibody-based detection method. For example, the level of the biomarker may be determined using an enzyme-linked immunosorbent assay (ELISA). The ELISA may be a direct ELISA, a sandwich ELISA, a competitive ELISA, or a reverse ELISA. The detection method may be optical (i.e., colorimetric or fluorometric) or electrochemical. In specific embodiments, the biomarker(s) may be detected using a sandwich ELISA with colorimetric detection.

On other embodiments, the antibody-based detection method may comprise protein immunoprecipitation, immunoelectrophoresis, Western blotting, or protein immunostaining. In still other embodiments, the biomarker(s) levels may be quantitated using high performance liquid chromatography (HPLC) or liquid chromatography-mass spectrometry (LC/MS).

Step (c)

The next step of the method comprises performing an analysis of the level of the at least one biomarker to determine whether the animal is healthy, is predisposed or likely to develop a joint ailment, or has a joint ailment. The analysis comprises comparing the level of the at least one biomarker in the blood sample to joint ailment-positive and/or joint ailment-negative reference levels of the at least one biomarker. If the level of the at least one biomarker falls within the range of joint ailment-negative reference levels, then the animal is healthy and does not have a joint ailment. If the level of the at least one biomarker falls within the range of joint ailment-positive reference levels, then the animal has a joint ailment. The severity of the joint ailment may be estimated based upon the level of the at least one biomarker. The progression of the joint ailment may be monitored by comparing the level of the at least one biomarker over time.

In some embodiments, the levels of two biomarkers may be determined. For example, the levels of osteocalcin and CTX1 may be determined and/or the ratio of osteocalcin/CTX1 may be determined. Alternatively, the levels of P2CP and C2C may be determined and/or the ratio of P2CP/C2C may be determined. In other embodiments, the levels of three biomarkers may be determined. In additional embodiments, the levels of four biomarkers may be determined. In still other embodiments, the levels of all five biomarkers may be determined.

Animals

Suitable animals include, but are not limited to, livestock animals, companion animals, lab animals, and zoological animals. In specific embodiments, the animal may be a livestock animal. Non-limiting examples of suitable livestock animals may include pigs, cows, poultry, goats, sheep, llamas, alpacas, aquatic animals, etc. In exemplary embodiments, the animal may be a pig, e.g., a sow. In other embodiments, the animal may be a dairy cow.

In other embodiments, the animal may be a companion animal. Non-limiting examples of companion animals may include pets such as dogs, cats, horses, rabbits, birds, or rodents (e.g. mice, rats, hamsters, guinea pigs). In yet other embodiments, the animal may be a zoological animal. As used herein, a "zoological animal" refers to an animal that may be found in a zoo. Such animals may include non-human primates, large cats, wolves, bears, hippos, kangaroos, etc. In still other embodiments, the animal may be a laboratory animal. Non-limiting examples of a laboratory animal may include rodents, canines, felines, and non-human primates.

(III) Methods for Treating or Preventing Joint Ailments

Another aspect of the present disclosure provides methods for treating or preventing joint aliments in animals. The methods may also be used to monitor the efficacy of the treatment method, wherein the treatment method may be modified accordingly. The methods comprise (a) collecting a blood sample from the animal, (b) determining the level of at least one of the biomarkers disclosed herein that is present in the blood sample; (c) performing an analysis of the level of the at least one biomarker to determine whether the animal has or is predisposed to having a joint ailment, wherein the analysis includes comparing the levels of the at least one biomarker in the blood sample to joint ailment-positive and/or joint ailment-negative reference levels of the at least one biomarker in order to determine if the animal has or is predisposed to having a joint ailment; and (d) administering an effective amount of a metal chelate to the animal if the animal is determined to have or to be predisposed to having a joint ailment.

Steps (a), (b), and (c) of the method are as described above in section (II), as are suitable joint ailments and animals.

Step (d)

If, at step (c), the animal is determined to have or to be predisposed to having a joint ailment, the next step comprises administering an effective amount of a metal chelate to the animal.

The metal chelate comprises at least one ligand and at least one metal ion. The ligand may be an amino acid, a hydroxy acid (e.g., alpha hydroxy acid), an organic acid, a sugar alcohol, protein, protein hydrolysate (e.g., soy protein hydrolysate), polysaccharide, or polynucleic acid.

In some embodiments, the ligand may be an amino acid. Suitable amino acid derivatives include alanate, arginate, asparaginate, aspartate, cysteinate, glutaminate, glutamate, histidinate, homocysteinate, isoleucinate, lysinate, methionate, phenylalinate, prolinate, serinate, threonate, typtophanate, tyrosinate, and valinate.

In other embodiments, the ligand may be an organic acid. Non-limiting examples of suitable organic acid moieties include adipate, ascorbate, caprylate, citrate, fulvate, furmarate, glucoheptonate, gluconate, glutarate, glycerophosphate, humate, lactate, ketoglutarate, malate, malonate, orotate, oxlate, pantothenate, picolinate, pidolate, sebacate, succinate, and tartrate.

In still other embodiments, the ligand may be a sugar alcohol. Suitable sugar alcohols include, without limit, sorbitol, mannitol, xylitol, lactitol, isomalt, maltitol, erythritol, and hydrogenated starch hydrolysates (HSH).

In specific embodiments, the ligand is a compound of Formula (I).

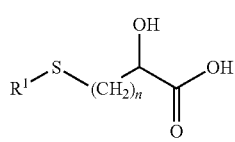
(I)

wherein $R^1$ is methyl or ethyl and n is 1 or 2. In exemplary embodiments, $R^1$ is methyl and n is 2 and the compound of Formula (I) is methionine hydroxy analog (or 2-hydroxy-4-(thiomethyl)butanoic acid, HMTBA).

The at least one metal ion may be calcium, chromium, cobalt, copper, germanium, iron, lithium, magnesium, manganese, molybdenum, nickel, potassium, sodium, rubidium, tin, vanadium, zinc, or combination thereof. In certain embodiments, the at least one metal ion may be calcium, chromium, cobalt, copper, iron, magnesium, manganese, nickel, potassium, sodium, zinc, or combination thereof. In specific embodiments, the at least one metal ion may be copper, manganese, zinc, or combination thereof.

The ratio of the at least one ligand and the at least one metal ion may vary in the metal chelate. For example, the ratio of ligand to metal may range from 1:1 to about 3:1 or higher. In embodiments in which the metal ion is divalent, the ratio of ligand to metal may be 2:1.

In particular embodiments, the metal chelate may comprise methionine hydroxy analog copper (i.e., MHA-Cu to $(HMTBA)_2$-Cu), methionine hydroxy analog manganese (i.e., MHA-Mn or $(HMTBA)_2$-Mn), methionine hydroxy analog zinc (i.e., MHA-Zn or $(HMTBA)_2$-Zn), or a combination of any or all of the foregoing (which are available from Novus International, Inc., under the tradename MINTREX®).

The effective amount of the metal chelate that is administered to the animal can and will vary, depending for example upon the type and age of the animal and/or the severity of the joint ailment. Persons skilled in the art can readily determine the appropriate amount.

In general, the metal chelate is included in the feed rations of the animal. Feed rations typically are formulated to meet the nutrient and energy demands of a particular animal. The nutrient and energy content of many common animal feed ingredients have been measured and are available to the public. The National Research Council has published books that contain tables of common feed ingredients and their respective measured nutrient and energy content. Additionally, estimates of nutrient and maintenance energy requirements are provided for animals of different life stages, age, sex, or use. This information can be utilized by one skilled in the art to estimate the nutritional and maintenance energy requirements of animal and determine the nutrient and energy content of animal feed ingredients.

EXAMPLES

The following examples illustrate various embodiments of the present disclosure.

Example 1: Protocol Description

Two different models of lameness (naturally-occurring and chemically-induced) were evaluated in this study. In both models, objective measures of lameness (serum biomarkers, force-plate, thermal imaging) were compared to visual gait scoring. The study design was a 2×2 factorial arrangement consisting of two dietary treatments (chelated trace minerals vs inorganic trace minerals) and two populations of pigs (lame vs healthy non-lame). The chelated trace minerals (MTX) comprised methionine hydroxy analog (MHA) chelate (i.e., MHA-Cu, MHA-Mn, and/or MHA-Zn) and the inorganic trace minerals (ITM) comprised mineral sulfates.

Four groups of pigs (8 lame/8 non-lame per group) for a total of 32 lame/32 non-lame/64 total were fed the dietary treatments for a period of two months. For the naturally-occurring portion of the trial (Example 2), lameness measurements were taken at baseline (d0), month 1 (d28) and month 2 (d53). At the end of the 2-month period, only the healthy animals (n=8 per group; 4 on MTX and 4 on ITM) were then injected with sodium urate crystals (10 mg/mL and 0.2 mL injection volume) into the right rear distal interphalangeal joint (Example 3).

Most methods used for gait scoring are based on uneven or asymmetrical weight-bearing. As shown in Table 1, a 5-point scale (0-4) was used, with 4 being most severe.

TABLE 1

Scoring System for Subjective Lameness Evaluation

| Lameness Score | Description |
|---|---|
| 0 | Animal moves freely and used all 4 limbs and feet evenly |
| 1 | Animal shows weight-shifting activities away from affected limb upon standing but show no lameness of limping when walking |
| 2 | Animal obviously shifts weight away from affected limb when standing and shows limping or adaptive behavior when walking (e.g., head bob, quickened step on affected limb) |
| 3 | Animal is reluctant to stand and/or walk, obvious limp and adaptive behaviors when walking |
| 4 | Animal is non-weight bearing on the affected limb when either standing or walking |

The force-plate analysis quantifies the amount of force each limb applies to four separate loading cells. Two data points per second were captured over a 2-minute time duration. A lame animal typically bears less weight on the limb that is painful or structurally unsound.

Thermal imaging measures the heat emitted from a body surface as infrared radiation. Studies of clinical disease have shown that a difference greater than 1° C. between two of the same anatomical regions indicate an abnormality such as inflammation. The high degree of symmetry between the left and right side of an animal is a valuable asset in the diagnosis of a unilateral problem associated with lameness. Thus, these objective measures of lameness should correlate to the visual gait score, which is also based on asymmetrical weight-bearing.

All statistical analyses were performed with SAS using the pig as the experimental unit. All lameness measurements were analyzed using a two-way analysis of variance (ANOVA) to test the main effects of dietary treatment and healthy vs lame plus their interactions; differences in front vs rear limbs were also compared. In addition, data were also evaluated using a mixed model including day, lameness, dietary treatment, bodyweight, group and gender. Day was included as a repeated measure using an autoregressive covariance structure, and data collected the day before the start of the study were included as covariates (for force-plate data only).

Pearson correlation coefficients and regression analyses were used to explore the relationship between objective measurements vs the gait score.

Example 2. Biomarker Levels in Healthy and Naturally-Occurring Lame Animals

Serum biomarkers were measured at day 0, day 25 and day 53 (2 months) in healthy (H) and lame (L) animals (n=48). The levels of serum CTX1, osteocalcin (OC), C2C, P2CP, and CTX2 were measured by enzyme-linked immunosorbent assay (ELISA) according to the procedures described in the commercial kits (e.g., MyBiosource). The results are presented in Table 2.

TABLE 2

Biomarker Levels in Healthy and Naturally-Occurring Lame Animals

|  | P2CP/C2C ratio | OC/CTX1 ratio | P2CP/CTX2 ratio | CTX1 | OC | P2CP | CTX2 | C2C |
|---|---|---|---|---|---|---|---|---|
| ITM | 1.32 | 15.2 | 1.08 | 15.45 | 161.5 | 7.28 | 7.41 | 14.09 |
| MTX | 1.04 | 15.2 | 1.27 | 16.58 | 163.2 | 8.28 | 6.95 | 14.63 |
| SEM | 0.14 | 0.98 | 0.06 | 0.54 | 3.70 | 0.28 | 0.24 | 0.47 |
| Group | <.0001 | <.0001 | <.0001 | <.0001 | <.0001 | <.0001 | <.0001 | <.0001 |
| Gender | 0.5349 | 0.7119 | 0.0007 | 0.1197 | 0.9446 | 0.0047 | 0.0020 | 0.0330 |
| H or L | 0.0890 | 0.8477 | 0.0908 | 0.0073 | 0.8430 | 0.2020 | 0.0002 | 0.0176 |
| Trt[1] | 0.1686 | 0.9498 | 0.0267 | 0.1398 | 0.7454 | 0.0114 | 0.1694 | 0.4124 |
| H or L*Trt | 0.2736 | 0.4433 | 0.1480 | 0.1134 | 0.1397 | 0.9727 | 0.7631 | 0.5731 |
| Day | 0.3520 | 0.0773 | 0.7891 | <.0001 | 0.2912 | 0.9771 | 0.4635 | 0.4111 |
| Trt*day | 0.4409 | 0.5765 | 0.4150 | 0.3543 | 0.9514 | 0.8792 | 0.3368 | 0.2474 |

|  | P2CP/CTX2 | | | | OC/CTX1 | |
|---|---|---|---|---|---|---|
| H or L | ratio | CTX2 | C2C | Day | ratio | CTX1 |
| Healthy (H) | 1.25 | 6.53 | 13.57 | 0 | 13.0 | 18.3 |
| Lame (L) | 1.11 | 7.82 | 15.15 | 28 | 16.3 | 14.1 |
| SEM | 0.06 | 0.24 | 0.47 | 56 | 16.3 | 15.5 |
| % delta | 11.2 | 16.5 | 10.4 | SEM | 1.2 | 0.66 |

[1]Treatment (ITM or MTX).

These results reveal that the biomarkers were able to distinguish between healthy vs lame, as well as demonstrate beneficial effects of MTX. Cartilage degradative markers, CTX2 (P=0.0002) and C2C (P=0.0176) were elevated and the ratio of cartilage synthesis/degradation (P2CP/CTX2; P=0.0908) was decreased in lame animals (Table 2). Dietary treatment differences were also observed: cartilage synthesis biomarker (P2CP, P=0.0114) and the ratio of cartilage synthesis/degradation (P2CP/CTX2, P=0.0267) were increased with MTX (Table 2). As shown in FIG. 1, there was not a diet (ITM vs MTX)*healthy vs lame interaction (P=0.9727). This indicates that MTX treatment is increasing cartilage synthesis in both healthy and lame pigs and may have preventative joint health effects.

Example 3: Urate-Induced Lameness

At the end of two months, sodium urate crystals (10 mg/mL and 0.2 mL injection volume) were injected into the right rear distal interphalangeal joint of healthy pigs from each of the four groups. Thus, a total of 16 pigs for MTX, and 16 for ITM were evaluated during the urate-induced portion of the trial. Data collection, relative to time of urate injection, occurred at baseline (d−1/d 53), 6 and 12 hr (d0/d54), 24 hr (d1/55), 48 hr (d2/56), 72 hr (d3/57) and 144 hr (d6/60) post-injection.

Figure 2:
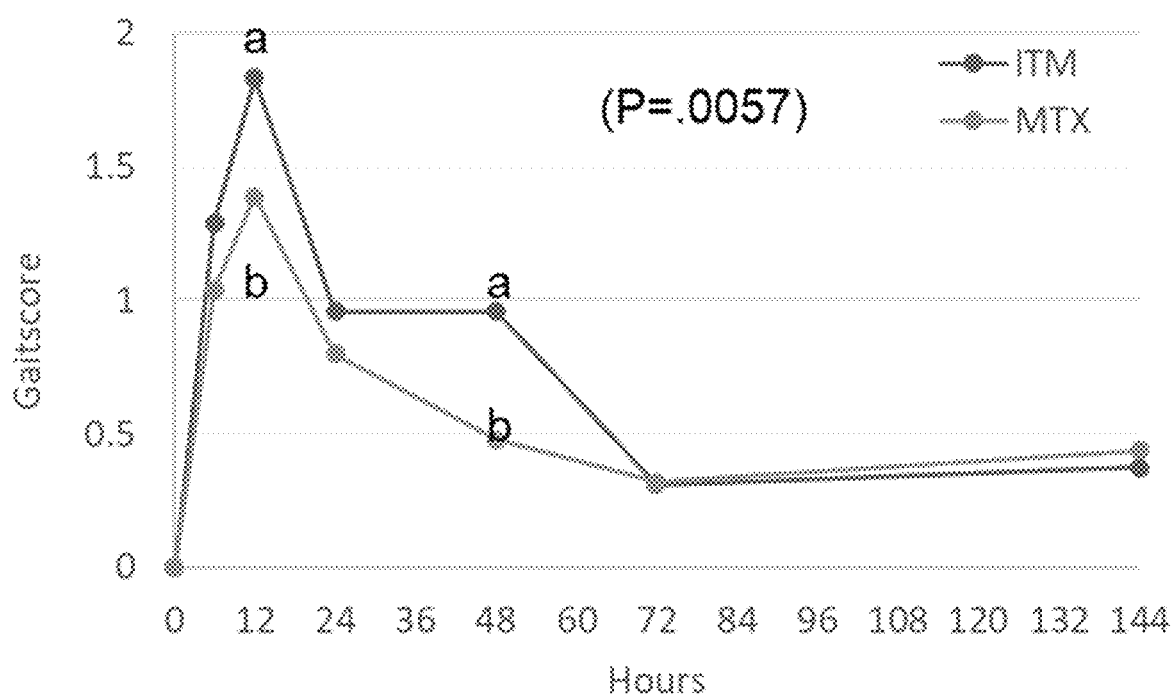
FIG. 2 presents a time-course of visual gait scores following urate injection to induce acute lameness. Presented are the gait scores for urate-injected animals fed MTX or ITM for two months prior to the injection.

As shown in FIG. 2, pigs fed MTX had lower gait scores (Main effect of diet: P=0.0057). In addition, gait scores at peak lameness (12 hr post-urate injection P=0.0244, 48 hr post-urate injection P=0.0155) were lower in pigs fed MTX. Since the pigs had been on the dietary treatments (MTX vs ITM) for 2 months prior to urate-injections, these findings suggest that MTX supplementation lowers the severity of urate-induced lameness.

Figure 3A:
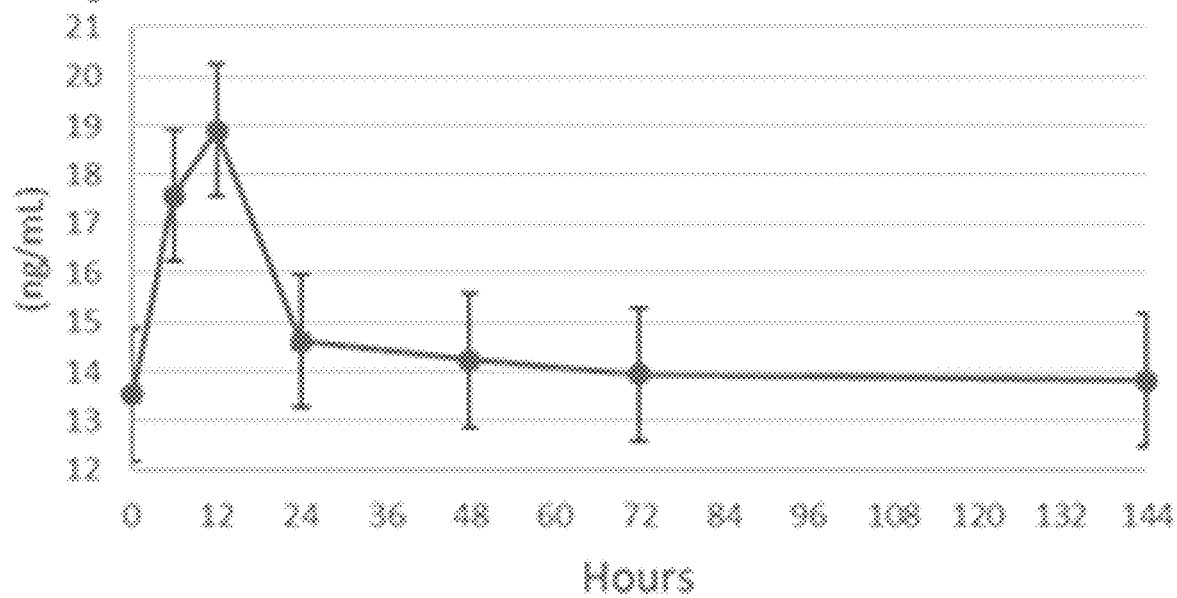
FIG. 3A presents a time-course of serum levels of C2C in urate-injected animals.
Figure 3B:
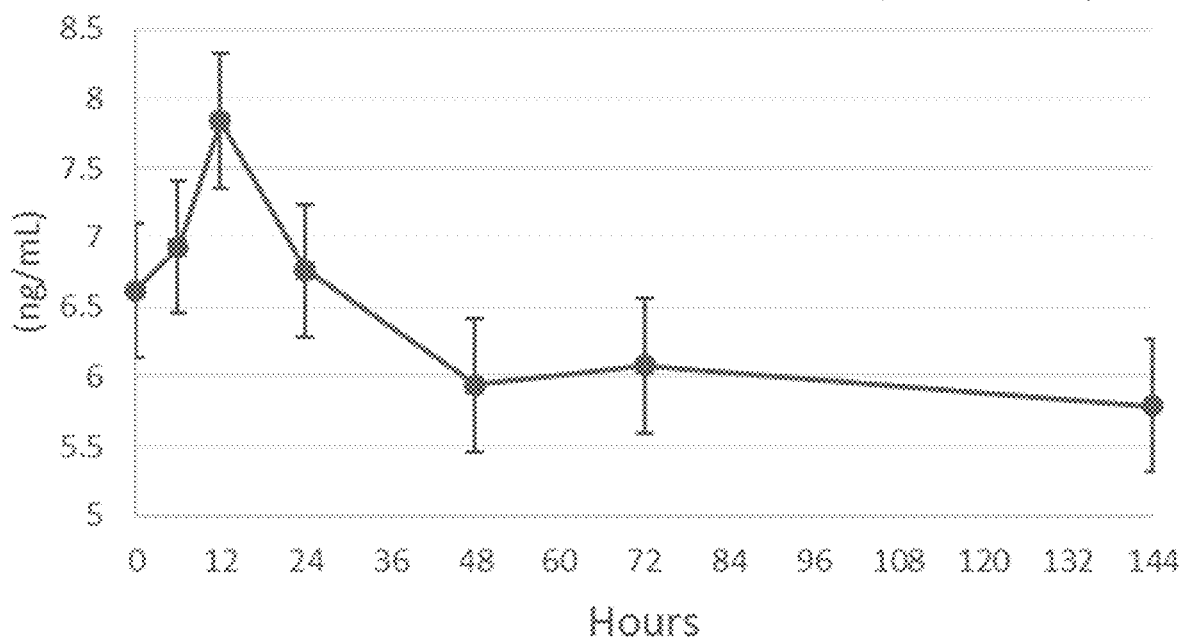
FIG. 3B plots a time-course of serum levels of CTX2 in urate-injected animals.
Figure 3C:
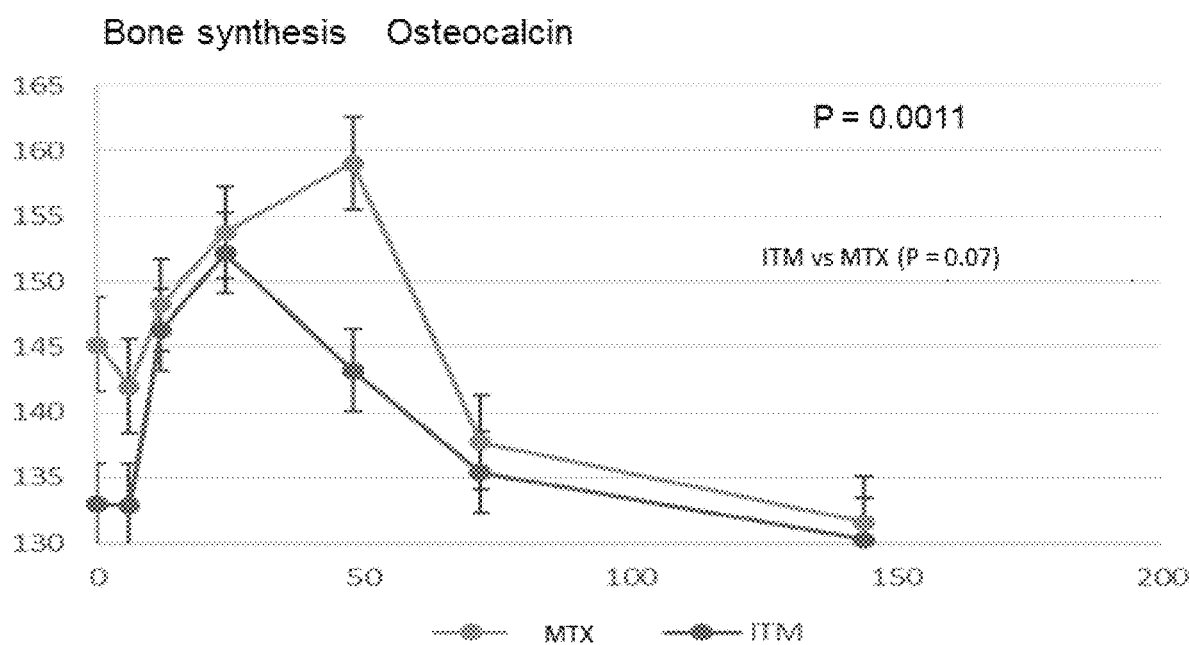
FIG. 3C presents a time-course of serum levels of osteocalcin in urate-injected animals previously fed MTX or ITM.

The time-course for the serum biomarkers after urate administration is shown in FIG. 3A-3C. Biomarker changes closely paralleled the changes in gait score. For example, cartilage degradative biomarkers (C2C and CTX2), similar to gait score, peaked 12 hr post-urate injection (FIG. 3A, 3B), bone synthesis biomarker (osteocalcin) peaked between 12 and 48 hr post-urate injection (FIG. 3C). Similar to gait scores, after 72 hr (if not sooner) these three biomarkers (C2C, CTX2, osteocalcin) returned to baseline or plateaued relative to initial concentrations.

Tables 3-5 present the biomarker levels after urate administration (without covariate). There were numerical or significant effects of time (Hr) for C2C (P=0.0853), CTX2 (P=0.1014), and osteocalcin (OC, P=0.0011) as indicated in FIG. 3A-3C. Beneficial effects of MTX were also observed; bone synthesis biomarker (OC, P=0.0700) and the ratio of bone synthesis/degradation (OC/CTX1; P=0.0470) were increased and the ratio of cartilage synthesis/degradation (P2CP/C2C; P=0.0990) was decreased with MTX.

TABLE 4

Time Course of Select Biomarkers

| Hour | C2C | CTX2 | OC | OC (ITM) | OC (MTX) |
|---|---|---|---|---|---|
| 0 | 9.73 | 11.17 | 139.1 | 133 | 145.2 |
| 6 | 10.15 | 12.27 | 137.5 | 133.0 | 142 |
| 12 | 12.84 | 13.06 | 147.2 | 146.3 | 148.2 |
| 24 | 9.48 | 10.93 | 153.0 | 152.2 | 153.8 |
| 48 | 9.23 | 10.49 | 151.2 | 143.2 | 159.1 |
| 72 | 9.58 | 10.39 | 136.5 | 135.4 | 137.7 |
| 144 | 9.15 | 10.52 | 130.95 | 130.3 | 131.6 |
| SEM | 0.8 | 0.59 | 4.0 | 4.0 | 4.0 |
| P value | 0.0853 | 0.1014 | 0.0011 | | |

TABLE 5

Gender and Biomarker Levels

| Gender | C2C | CTX2 | P2CP | P2CP/CTX2 ratio |
|---|---|---|---|---|
| Barrow | 10.8 | 12.6 | 7.13 | 1.07 |
| Gilt | 9.2 | 9.6 | 6.31 | 1.21 |
| SEM | 0.42 | 0.36 | 0.17 | 0.06 |
| P value | 0.0053 | <0.0001 | 0.0011 | 0.0835 |

Although it was predicted that both bone and cartilage synthesis/degradation would increase with MTX, based on correlation analyses, bone and cartilage syntheses were negatively correlated (Table 6 and opposite slopes for osteocalcin (+) and P2CP (−) in Table 7). Similarly, a negative direction between bone and cartilage synthesis was reported by Billinghurst et al. (Am J Vet Res, 2004, 65(2):143-50) in foals with osteochondrosis (e.g., decreased osteocalcin and increased P2CP).

TABLE 6

P2CP is Negatively Correlated to Osteocalcin

| Model | Bone synthesis marker | Cartilage synthesis marker | Correlation coefficient | P-value |
|---|---|---|---|---|
| Urate-induced | Osteocalcin | P2CP | −0.2898 | 0.0007 |
| Naturally-occurring | Osteocalcin | P2CP | −0.3813 | 0.0116 |

TABLE 3

Biomarker Levels as Affected by Urate-induced Lameness

| | P2CP/C2C ratio | P2CP/CTX2 ratio | OC/CTX1 ratio | C2C | CTX2 | P2CP | OC | CTX1 |
|---|---|---|---|---|---|---|---|---|
| ITM | 1.67 | 1.11 | 11.13 | 9.72 | 11.10 | 6.67 | 139.1 | 18.6 |
| MTX | 0.89 | 1.17 | 13.70 | 10.33 | 11.42 | 6.77 | 145.3 | 18.9 |
| SEM | 0.34 | 0.06 | 0.92 | 0.42 | 0.36 | 0.17 | 2.5 | 0.57 |
| Grp | <0.0001 | <0.0001 | <0.0001 | <0.0001 | <0.0001 | <0.0001 | <0.0001 | <0.0001 |
| Gender | 0.5818 | 0.0835 | 0.4405 | 0.0053 | <0.0001 | 0.0011 | 0.9614 | 0.6233 |
| Trt | 0.0990 | 0.4955 | 0.0470 | 0.2960 | 0.5168 | 0.6921 | 0.0700 | 0.6233 |
| Hr | 0.7260 | 0.1063 | 0.3021 | 0.0853 | 0.1014 | 0.3398 | 0.0011 | 0.3205 |
| Hr*Trt | 0.6260 | 0.426 | 0.3950 | 0.7466 | 0.9413 | 0.9822 | 0.8181 | 0.8439 |

TABLE 7

Biomarkers are Correlated to Gait Score

| Marker | Expected Direction | Slope | P-value |
|---|---|---|---|
| Degradative | | | |
| CTX2 | ↑ | +0.9 | NS |
| C2C | ↑ | +1.4 | 0.0072 |
| CTXI | ↑ | +5.9 | <0.0001 |
| Synthesis | | | |
| P2CP | ↑↓ | −0.38 | 0.0914 |
| Osteocalcin | ↑↓ | +26.1 | 0.0070 |
| Ratio of Synthesis/Degradative | | | |
| P2CP/CTX2 | ↓ | −0.27 | 0.0010 |
| P2CP/C2C | ↓ | −0.87 | 0.0716 |
| Osteocalcin/CTXI | ↓ | −4.8 | 0.0138 |

As shown in Table 7, for the urate-induced lameness model, correlation and regression analyses demonstrated that biomarkers were significantly correlated to lameness or gait score. Out of the 8 biomarkers evaluated, five were significantly correlated at P<0.05; two at P<0.10; only one was not significant. Furthermore, the slopes were in the expected direction: positive for cartilage and bone degradative markers, negative for the ratio of synthesis/degradation in bone and cartilage and mixed for synthetic markers (positive slope for osteocalcin; negative slope for P2CP).

Figure 4A:
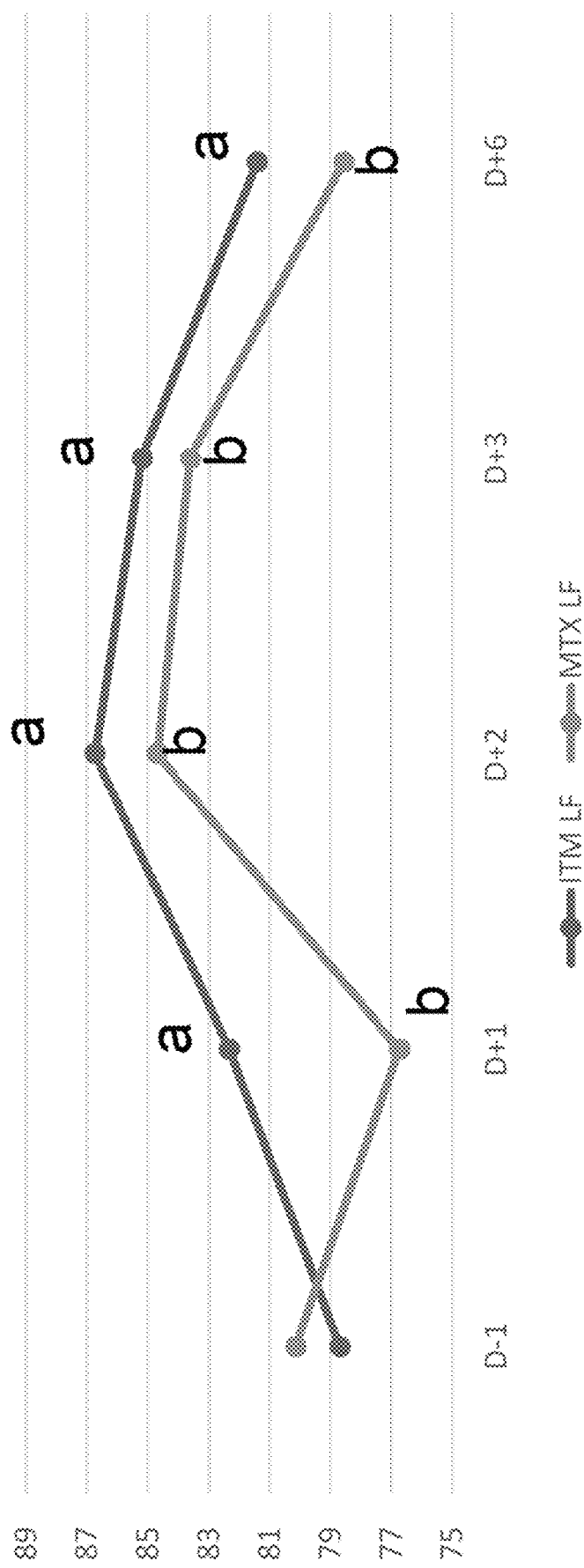
FIG. 4A presents the average weight borne by the front contralateral leg of MTX and ITM animals over time.
Figure 4B:
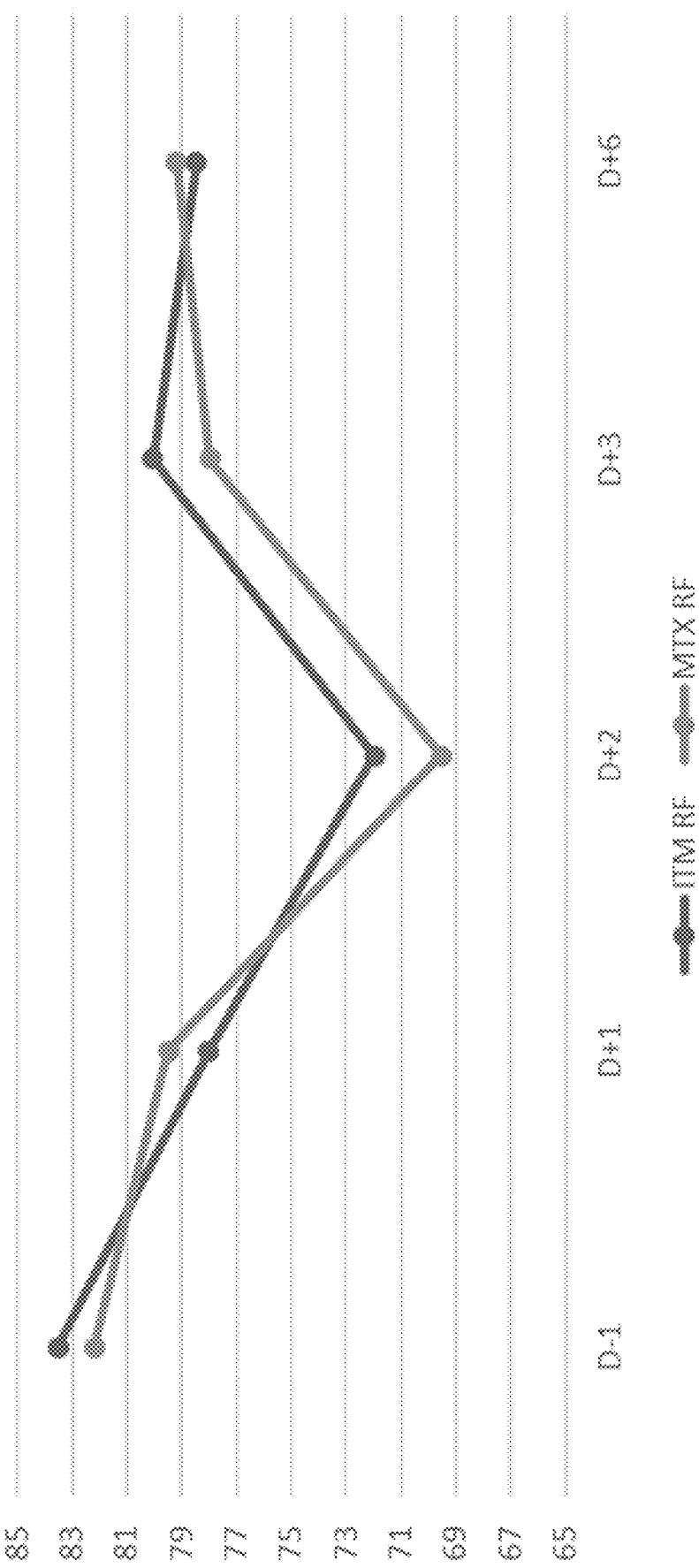
FIG. 4B shows the average weight borne by the front ipsilateral leg of MTX and ITM animals over time.
Figure 4C:
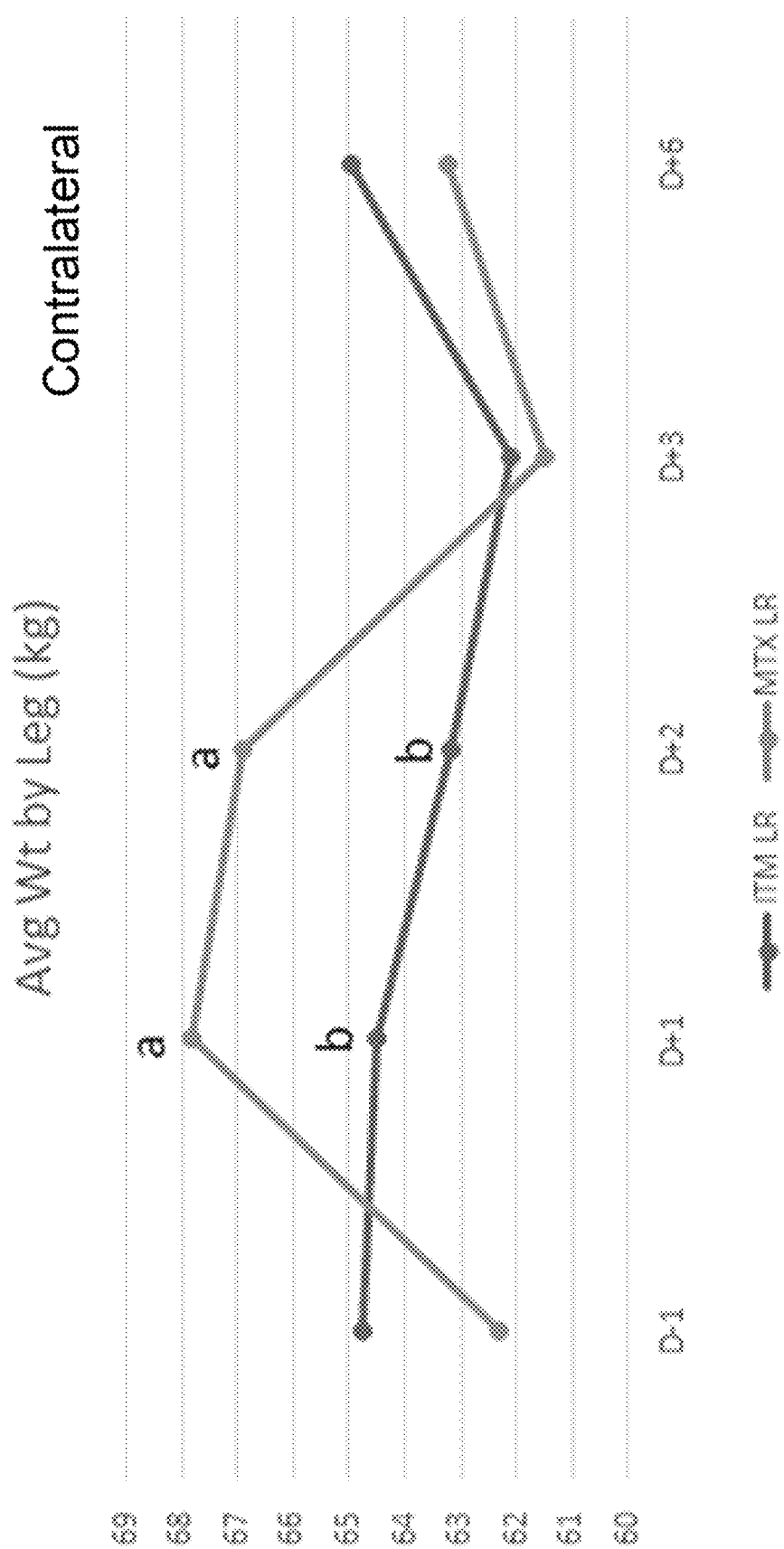
FIG. 4C presents the average weight borne by the rear contralateral leg of MTX and ITM animals over time.
Figure 4D:
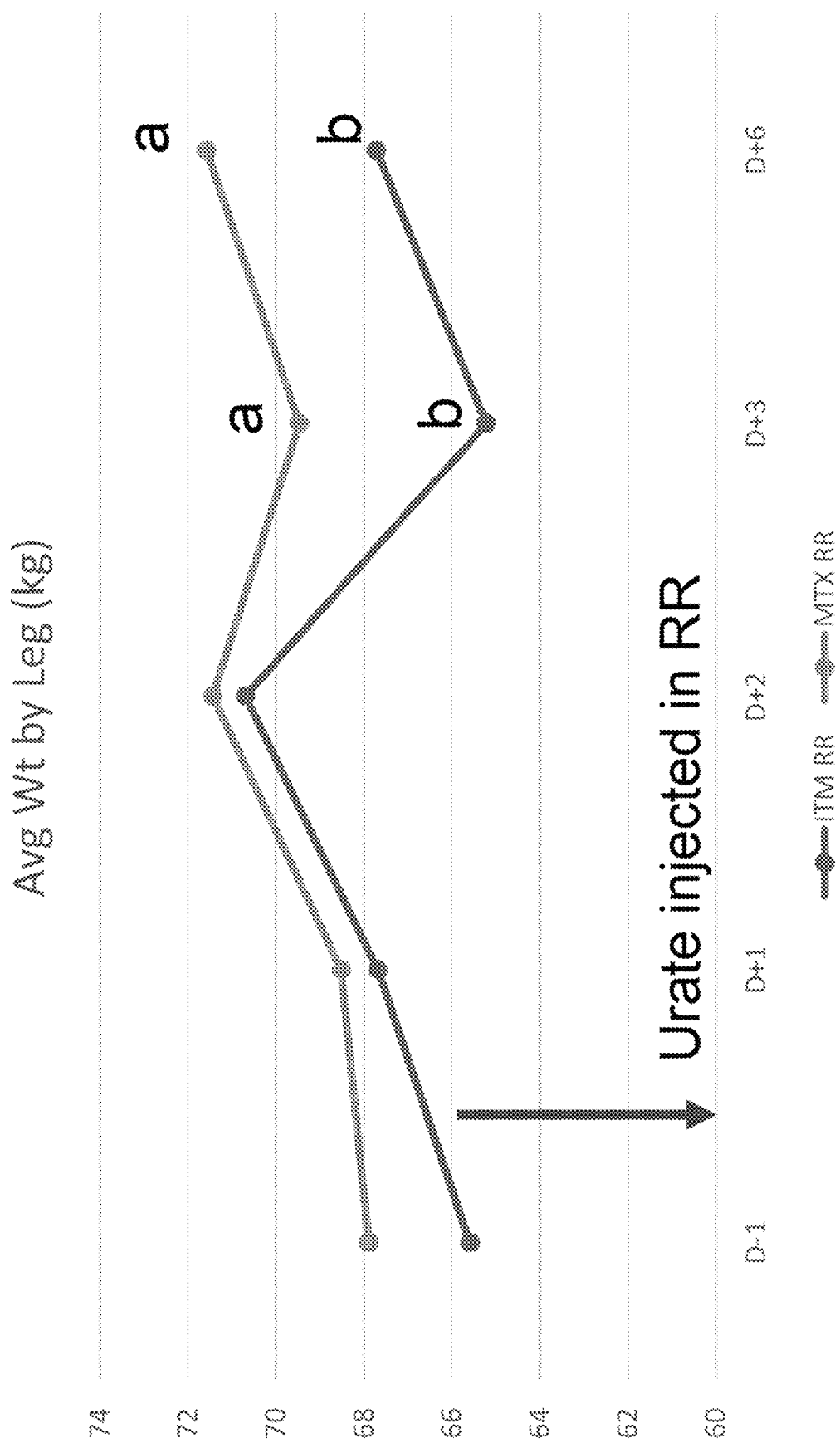
FIG. 4D shows the average weight borne by the urate-injected leg of MTX and ITM animals over time.

Force-plate analyses are presented in FIG. 4A-4D. These analyses also demonstrated beneficial effects of MTX on weight-bearing. For the urate-injected foot (right rear, RR), higher weight-bearing occurred at all timepoints post-injection in MTX animals (FIG. 4D; significantly higher at D+3 and D+6). Higher weight-bearing also occurred on the contralateral rear leg in MTX animals (FIG. 4C; higher at D+1 and D+2 post-injection). These findings suggest that the lameness was less severe in pigs fed MTX, which agreed with the gait score findings (FIG. 2; gait score was less severe for MTX-fed pigs).

Taken together, serum biomarkers for cartilage degradation (C2C, CTX2) were increased and bone synthesis biomarker (osteocalcin) were altered in lame pigs. Those biomarkers can be used objectively to measure lameness in pigs. Feeding MTX improved metabolism of bone and cartilage by increasing both bone synthesis (osteocalcin) over degradation (osteocalcin/CTX1 ratio) and cartilage synthesis (P2CP) over degradation (P2CP/CTX2 ratio). In summary, lameness increased cartilage degradation biomarkers and altered bone synthesis biomarkers, feeding MTX improved bone and cartilage synthesis over degradation, therefore reducing lameness.

What is claimed is:

1. A method for treating mild, naturally-occurring lameness in a pig, the pig having a gait score of about 1 or less on a 5 point scale, the method comprising:
   (a) determining the level of at least two biomarkers in a blood sample from the pig, the at least two biomarkers comprising C-terminal telopeptide of type II collagen (CTX-2) and type II collagen cleavage (C2C);
   (b) comparing the level of the at least two biomarkers of the pig to a non-lame pig having a gait score of about 0 on a 5 point scale to determine whether the pig is mildly lame, wherein the pig is mildly lame if the level of CTX-2 and C2C is increased compared to the non-lame pig; and,
   (c) administering an effective amount of a metal chelate to the pig if the pig is determined to be mildly lame, wherein the administering results in a decrease of the level of C2C and CTX-2.

2. The method of claim 1, wherein step (b) comprises an antibody-based detection method.

3. The method of claim 1, wherein the metal chelate comprises at least one metal ion and at least one ligand, wherein the at least one ligand is an amino acid, hydroxy acid, organic acid, sugar alcohol, protein, protein hydrolysate, polysaccharide, or polynucleic acid.

4. The method of claim 3, wherein the at least one metal ion is calcium, chromium, cobalt, copper, iron, magnesium, manganese, nickel, potassium, sodium, zinc, or combination thereof.

5. The method of claim 3, wherein the at least one ligand is a compound of Formula (I):

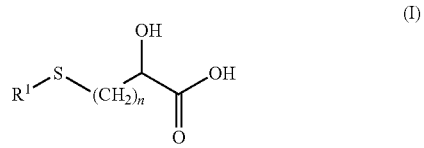

wherein:
R$^1$ is methyl or ethyl; and
n is 1 or 2.

6. The method of claim 5, wherein R$^1$ is methyl and n is 2.

7. The method of claim 6, wherein the at least one metal ion is copper, manganese, zinc, or combination thereof.

8. The method of claim 1, wherein the at least two biomarkers further comprise procollagen type II C-terminal propeptide (P2CP).

* * * * *